US00PP22745P2

(12) United States Plant Patent
Niekerk

(10) Patent No.: US PP22,745 P2
(45) Date of Patent: May 22, 2012

(54) ***HEBE* PLANT NAMED 'WILD ROMANCE'**

(50) Latin Name: ***Hebe* hybrid**
Varietal Denomination: Wild Romance

(76) Inventor: Johan Van Niekerk, Waddinxveen (NL)

( * ) Notice: Subject to any disclaimer, the term of this patent is extended or adjusted under 35 U.S.C. 154(b) by 0 days.

(21) Appl. No.: 13/068,178

(22) Filed: May 4, 2011

(51) Int. Cl.
*A01H 5/00* (2006.01)

(52) U.S. Cl. ..... Plt./251

(58) Field of Classification Search ..... Plt./251
See application file for complete search history.

(56) References Cited

OTHER PUBLICATIONS

Wild Romance *Hebe* The Garden Centre Group, retrieved from the Internet at <http://www.thegardencentregroup.co.uk/item/Evergreen-Shrubs/Wild-Romance/SYD>, 2011 retrieved on Dec. 12, 2011, 2 pages.*

* cited by examiner

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Hebe*, 'Wild Romance', characterized by its exhibits foliage that is dark red in spring, its leaves that are long in length and elliptic in shape, its open plant habit, and its vigorous growth habit.

2 Drawing Sheets

Botanical classification: *Hebe* hybrid.
Cultivar designation: 'Wild Romance'.

BACKGROUND OF THE INVENTION

The present invention relates to a new and distinct cultivar of *Hebe*, botanically of hybrid origin and known as *Hebe* 'Wild Romance' and will be referred to hereafter by its cultivar name. 'Wild Romance'. 'Wild Romance' is grown for use as a container plant and as a landscape shrub.

The new cultivar was discovered by the Inventor as a naturally occurring chimeral mutation of *Hebe* 'Bronzy Baby ' (not patented) that was growing in a container block at the Inventor's nursery in March of 2005 in Waddinxveen, The Netherlands.

Asexual reproduction of the new cultivar was first accomplished by the inventor using terminal stem cuttings in Waddinxveen, The Netherlands in October of 2005. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Wild Romance' as it new and distinct cultivar of *Hebe*.

1. 'Wild Romance' exhibits foliage that is dark red in spring.
2. 'Wild Romance' exhibits leaves that are long in length and elliptic in shape.
3. 'Wild Romance' exhibits on open plant habit.
4. 'Wild Romance' exhibits a vigorous growth habit.

'Wild Romance' can be compared to its parent plant, 'Bronzy Baby'. 'Bronzy Baby' differs from 'Wild Romance' in having bronze colored foliage in spring, in having leaves that are smaller in size and lanceolate in shape, and in having a more compact plant habit. 'Wild Romance' can be compared to the cultivars 'Magic Summer' (U.S. Plant Pat. No. 20,359) and 'Neprock' (not patented). 'Magic Summer' differs from 'Wild Romance' in having a more compact habit, in having a less vigorous plant habit and in having foliage that is suffused with purple in spring rather than deep red. 'Neprock' differs from 'Wild Romance' in having foliage that is green with greenish yellow margins in color that lack any red coloration and in having a more vigorous growth habit.

BRIEF DESCRIPTION OF THE DRAWINGS

The accompanying colored photographs illustrate the overall appearance and distinct characteristics of the new *Hebe*. The photographs were taken of a plant approximately two years in age as grown in a 5-liter container outdoors in a cold-storey greenhouse in a 5-liter container in Hazerswoude-Dorp, The Netherlands.

The photograph in FIG. 1 is a side view of 'Wild Romance'.

Figure 1:
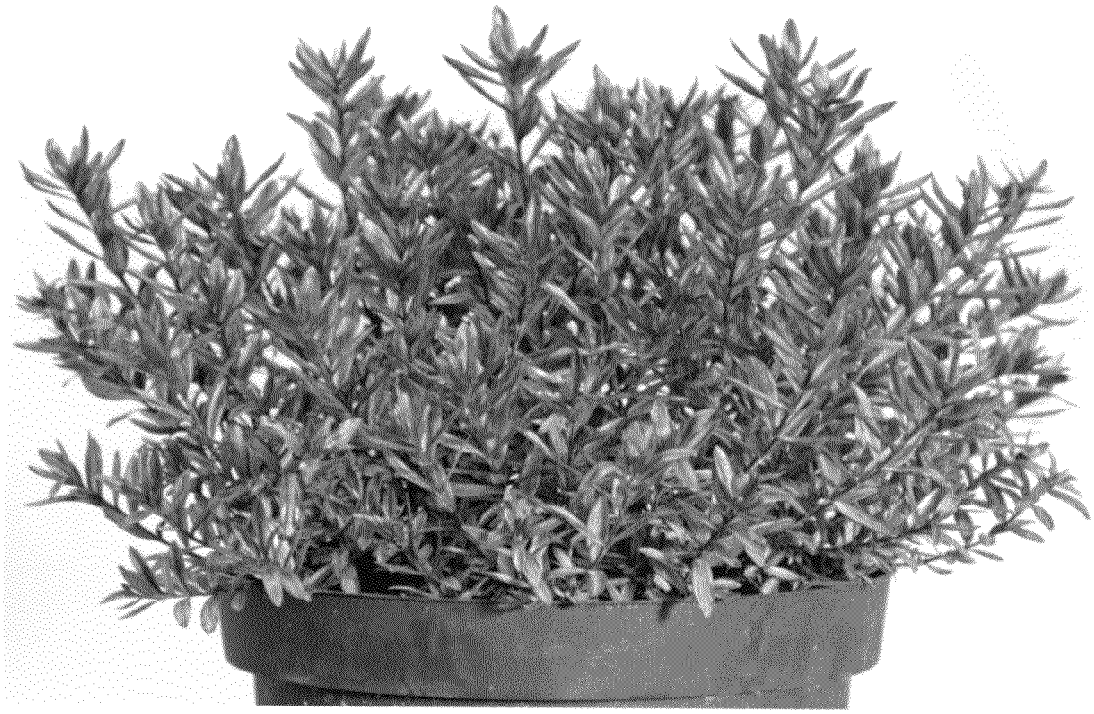
Figure 2:
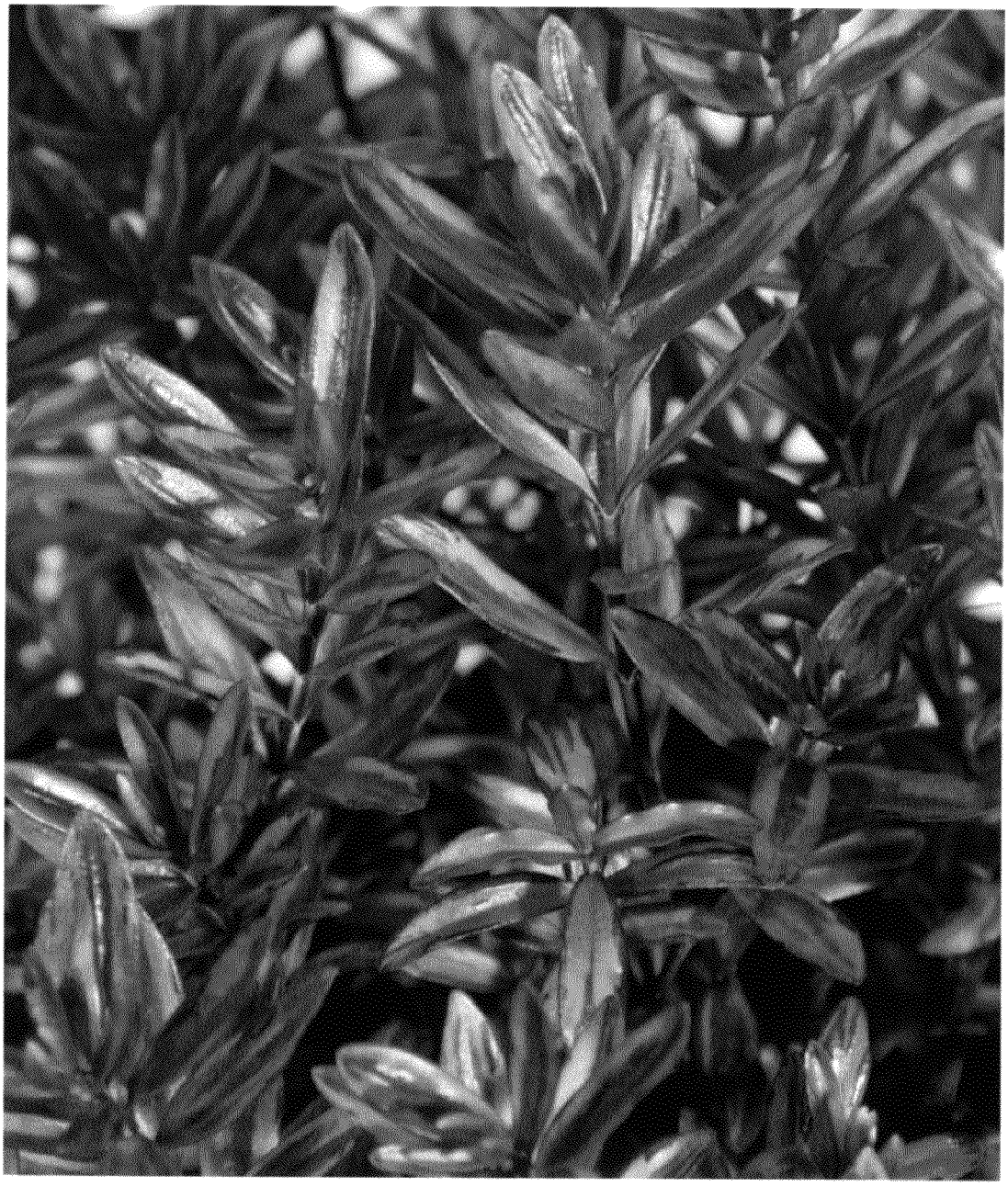

The photograph in FIG. 2 provides a close-up view of the spring foliage of 'Wild Romance'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of two-year-old plants of the new cultivar as grown in an unheated greenhouse in 5-liter containers in Hazerswoude-Dorp, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Perennial evergreen shrub.

*Plant habit*.—Broad, upright and spreading.

*Height and spread*.—Reaches about 22.7 cm in height and 35.9 cm in width.

*Hardiness*.—Tolerates temperatures up to at least 35° C. and is cold hardy to at least U.S.D.A. Zone 8.

*Disease resistance*.—Not more susceptible to pests and diseases than other *Hebe* varieties.

*Root description*.—Dense, fine, moderately fibrous.

*Growth rate*.—Vigorous, about 4 cm per month in the spring growth season.

*Propagation*.—Terminal stem cuttings.

Stem description:

*Stem size*.—Lateral branches are an average of 10.8 cm in length and 2 mm in width.

*Stem shape*.—Round.

*Stem color*.—N186C.

*Stem surface*.—Slightly glossy, sparsely covered with very short glandular hairs; average length of 0.25 mm, N155A in color.

*Internode length*.—Average of 1.3 cm.

*Branching habit*.—Freely branching, average of 100 lateral branches.

Foliage description:

*Leaf shape*.—Narrow elliptic and slightly concave.

*Leaf division*.—Simple.

*Leaf base*.—Cuneate.

*Leaf apex*.—Broad, bluntly acute.

*Leaf venation*.—Pinnate, only mid rib is conspicuous, a color between 147A and N189A on upper surface and N186C in color on lower surface.

*Leaf margins*.—Entire.

*Leaf attachment*.—Sessile.

*Leaf arrangement*.—Opposite.

*Leaf surface*.—Moderately glossy and smooth on upper and lower surface.

*Leaf color*.—Young upper surface; between N186C and 203B, margins 187D, mature upper surface; between 147A and N189A, margins 164C, young lower surface; N186C, margins ranging from 187B to 187C, mature lower surface; between N186C and 200A, margins 187C. Young leaves are produced in spring through summer with the same coloration, mature leaf color is present in summer, fall and winter.

*Leaf number*.—Average of 16 (8 pairs) per lateral branch.

*Leaf size*.—Average of 2.9 cm in length and 8.5 mm in width.

*Leaf aspect*.—Held slightly upwards to nearly horizontal to lateral branch.

*Leaf fragrance*.—None.

Flower description:

*Inflorescence type*.—Racemes of campanulate flowers, arranged at terminus and in opposite pairs at nodes. The new cultivar is primarily grown as a foliage plant but flowers can be observed on mature plants in the landscape.

*Flowering period*.—For about 6 weeks during mid summer in The Netherlands.

*Inflorescence size*.—Average of 5 cm in length (excluding peduncle) and 2.2 cm in width.

*Flower shape*.—Campanulate.

*Flower fragrance*.—Faint, fresh, pleasant, acidic.

*Flower quantity*.—Average of 80 per raceme, average of 20 racemes on a plant 4 years-old as grown in the landscape.

*Flower arrangement*.—Packed tightly in a whorl on peduncle with flowers opening from the base towards the apex.

*Flower aspect*.—Held outward.

*Flower lastingness*.—Individual flowers last about 7 days, about 25% of flowers of raceme are open at one time, self cleaning.

*Flower size*.—Average of 1 cm in depth and 8 mm in diameter.

*Peduncles*.—Average of 6.2 cm in length and 1 mm in width, 177B in color, surface is covered with very short hairs, round in shape, held at about a 40° angle to stem.

*Pedicels*.—Average of 1.5 mm in length and 0.5 mm in width, held at about a 45° angle to peduncle, 183C in color, surface is glabrous.

*Flower buds*.—Narrowly elliptical in shape, average of 5 mm in length and 2 mm in diameter, 90B in color blushed at apex with N155A with calyx portion 150C.

*Calyx*.—Rotate, average of 3 mm in length and 2 mm in width.

*Sepals*.—4, narrowly ovate in shape, margin is entire, apex is acute, base is fused on lower 30%, upper and lower surface is glabrous and dull, color of upper and lower surface is 150C, average of 3 mm in length and 1 mm in width.

*Corolla*.—Campanulate with lower 50% of petal portion fused towards base.

*Petals*.—4, about 8 mm in length and 2.2 mm in width, lobes oblanceolate in shape, entire margins, apex of lobes obtuse, upper and lower surface is glabrous, color of upper surface when opening and fully open; N87B with throat N155A, color of lower surface when opening; N87D with fused base N155A, color of lower surface when fully open; N87B with fused base N155A, color of both surfaces after fading; 85A.

Reproductive organs:

*Gynoecium*.—1 Pistil, stigma is clavate in shape and N79B in color, style is about 7 mm in length and N80 in color, ovary is 150C in color.

*Androcoecium*.—2 stamens, anthers are elliptic in shape and dorsifixed, about 0.5 mm in length and N79B in color, filaments are about 6 mm in length and 92A in color, pollen is minimal in quantity and 8D in color.

*Fruit and seed*.—Seed production has not been observed.

It is claimed:

1. A new and distinct cultivar of *Hebe* plant named 'Wild Romance' as herein illustrated and described.

* * * * *